United States Patent [19]
Elder

[11] Patent Number: 5,750,883
[45] Date of Patent: May 12, 1998

[54] METHOD AND APPARATUS FOR DETERMINING THE SALT CONTENT OF SNACK FOODS

[75] Inventor: Vincent A. Elder, Carrollton, Tex.

[73] Assignee: Recot, Inc., Pleasanton, Calif.

[21] Appl. No.: 747,367

[22] Filed: Nov. 12, 1996

[51] Int. Cl.[6] .......................... G01N 33/06; G01N 15/00
[52] U.S. Cl. .................. 73/53.01; 73/61.48; 73/61.41; 73/61.71; 426/560; 426/804; 426/808
[58] Field of Search ................ 73/53.01, 61.48, 73/61.41, 61.71, 53.02, 863.91; 426/250, 560, 804, 806, 808

[56] References Cited

U.S. PATENT DOCUMENTS

| | | | |
|---|---|---|---|
| 3,612,887 | 10/1971 | Carnevari et al. | 250/219 Q |
| 3,876,805 | 4/1975 | Craig et al. | 426/23 |
| 4,252,018 | 2/1981 | Neises | 73/421 A |
| 4,289,020 | 9/1981 | Paap | 73/61.1 R |
| 4,607,536 | 8/1986 | Lawson et al. | 73/863.91 |
| 4,908,221 | 3/1990 | Barrett | 426/240 |
| 5,251,475 | 10/1993 | Kanzaki et al. | 73/61.41 |
| 5,338,560 | 8/1994 | Wesdorp et al. | 426/573 |
| 5,366,755 | 11/1994 | Timonen et al. | 426/658 |
| 5,400,382 | 3/1995 | Welt et al. | 378/69 |

*Primary Examiner*—Hezron E. Williams
*Assistant Examiner*—J. David Wiggins
*Attorney, Agent, or Firm*—Jones, Day, Reavis & Pogue

[57] ABSTRACT

A method and apparatus for determining the salt content of snack foods by X-ray radiation backscatter. The snack food is irradiated with low-energy X-ray radiation in the range of from about 4 keV to about 12 keV. A detector of backscatter radiation is placed above the snack food at a distance in the range of from about 2 inches up to about 8 inches. The detected X-ray backscatter radiation intensity from the snack food is found at an energy level above the kilo-electron volts range of chlorine X-rays. The detected X-ray backscatter radiation intensity is representative of the snack food salt content and can be used to adjust the amount of salt or seasoning containing salt being applied to snack foods in a continuous on-line process.

19 Claims, 5 Drawing Sheets

METHOD AND APPARATUS FOR DETERMINING THE SALT CONTENT OF SNACK FOODS

BACKGROUND OF THE INVENTION

1. Field of the Invention

The present invention relates in general to the measurement of salt in snack foods and in particular to a process and apparatus for on-line measurement in snack foods using X-ray absorption or reduction in backscatter radiation.

2. Description of Related Art Including Information Disclosed Under 37 CFR 1.97 AND 1.98

It is well known in the prior art to use X-ray absorption and radiation backscatter intensity to measure salt content in a product. In U.S. Pat. No. 4,506,543, a method of determining the concentration of two salts in a liquid medium is disclosed. X-ray absorption is used as one of the elements to determine the respective concentrations. Thus it uses the absorption of X-rays in conjunction with sound velocity and temperature measurements to determine the concentrations of two salts in a liquid medium.

In U.S. Pat. No. 4,266,425, a method is disclosed for continuously determining the composition and mass flow of butter and similar substances including calculating the salt content. However, in order to determine the salt content brought into the butter from the brine, the flow rate of the brine is measured at a valve introducing the brine into the manufacturing process. A signal representing the flow rate is transmitted to a computer and since the brine has a known salt content, the flow rate together with the mass flow rate of the butter indicates the amount of salt being introduced into the butter. A computer has a memory wherein calibration data from prior tests is stored. By comparing the calibration data with the measured X-ray backscatter intensity, the measured density, the known curd content, the velocity, and in the case of a salted substance, the brine flow, composition and mass flow of the substance may be calculated.

There are two basic techniques for quantitative measurements with X-rays, i.e. X-ray fluorescence and X-ray absorption. These techniques are described in standard analytical chemistry textbooks (p. 262–270 in *Instrumental Methods of Analysis, Sixth Edition*, 1981, by Hobart H. Willard, Lynne L. Merritt, Jr., John A. Dean, and Frank A. Settle, Jr., D., published by Van Nostrand Company). Salt (sodium chloride) in snack foods can be measured by X-ray fluorescence of chlorine. Characteristic X-rays of chlorine are produced when a sample containing salt is irradiated with X-rays of sufficient energy. Characteristic chlorine X-rays are relatively soft (low energy). The difficulties of measuring soft X-rays are well known because soft X-rays are absorbed by the sample itself, air, and detector windows. Although laboratory analyzers for measuring salt by chlorine X-ray fluorescence are commercially available, the limitations of soft chlorine X-rays are particularly difficult to overcome for non-destructive, on-line measurement of salty snack foods. First, the detectors of the on-line analyzer must be close to the moving sample bed. Since soft chlorine X-rays are absorbed by air, laboratory analyzers are frequently run under vacuum or purged with helium. Helium purge or maintaining a vacuum would be too expensive for an on-line analyzer. If helium or vacuum is not used, the detectors of the on-line analyzer must be close to the moving sample bed. A small distance between sample and detector is easy in a laboratory analyzer but is difficult to maintain for an on-line analyzer because of different product flows and different conveyor speeds. In the case of snack foods, which are generally deposited on a continuously moving conveyor in a substantially uniform layer as an on-line process, the detector must be close so that the chlorine X-ray intensity will not be critically diminished by absorption in the air. In this case, the detector is so close to the substantially uniform layer of snack food that, should the layer vary from its uniformity for whatever reason, the detector may physically engage the snack foods causing them to stack up. Thus, the use of this method has been limited because of the problems created in the physical operation of the device. Second, thin and fragile beryllium windows on the detectors are essential for chlorine X-rays because stronger and thicker detector windows would absorb the soft chlorine X-rays. Third, a proportional counter or a solid state detector with a multi-channel analyzer must be used for chlorine X-ray fluorescence. The proportional counter is an energy dispersive detector and the multichannel analyzer classifies each X-ray by energy level Characteristic chlorine X-rays are produced by irradiating the sample with higher energy X-rays. Since the chlorine X-rays are less intense than the irradiating X-rays, a proportional counter with multichannel analyzer is essential for measuring chlorine X-rays. The proportional counter or solid-state detectors are expensive and require preamplifiers and other electronics to function. Less expensive and more rugged Geiger counters cannot be used for chlorine X-rays because Geiger counters measure total counts and do not have multichannel capability. Fourth, chlorine X-rays are sensitive to temperature of the air and distance between the sample and detector because the air absorbs the chlorine X-rays.

Absorption or reduction in backscatter X-rays should be capable of measuring salt in snack foods, but such a technique has not been reported in the prior art. The elements of snack food are primarily light elements with low atomic number (carbon, hydrogen, oxygen, and nitrogen), which have high backscatter of X-rays. Salt (sodium and chlorine) has higher atomic number elements, which absorb X-rays and reduce backscatter X-rays. Reduction in backscatter X-rays can be used to measure salt on snack foods. In comparison with chlorine X-rays, absorption of backscatter X-rays by salt has several advantages for an on-line analyzer. First, backscatter X-rays have higher energy and are less absorbed by air than chlorine X-rays. Since backscatter X-rays are less absorbed by air, distance between the moving sample bed and the detectors can be larger. Second, temperature and distance effects are smaller with backscatter X-rays because of less absorption by air. Third, thicker and stronger detector windows can be used because backscatter X-rays are more penetrating than chlorine X-rays. Fourth, use of a less expensive and more rugged Geiger counter is possible with backscatter X-rays. Since backscatter X-rays are more intense than emitted fluorescence X-rays, a multichannel analyzer would not be needed. For a Geiger counter to work, the Geiger counter would have to be covered with a polymer or mica window that absorbed almost all of the chlorine X-rays while transmitting most of the backscatter X-rays.

There are several reasons that backscatter measurement of salt on snack foods has not been part of prior art. First, substantial averaging is needed to obtain accurate measurement with backscatter measurement. Continuous averaging is obtained for an on-line application with a continuously moving bed of chips of sliced food or snack food. Backscatter measurement of salt in snack foods would not work well with a laboratory analyzer which has limited averaging, and has, in fact, not been developed with a laboratory analyzer. Second, salt measurement of snack foods is more sensitive than liquid samples because all of the salt is on the surface of the snack food. Liquid samples are homogeneous, and the backscatter measurement is less sensitive. In U.S. Pat. No. 4,506,543, the lowest salt (sodium chloride) concentration measured in water was 10%. With salty snacks (corn chips and potato chips), the measured salt levels are always less than 2% by weight. Third, the elemental composition of the snack chips has to be relatively constant. If elements with higher atomic number vary enough, backscatter X-rays would be too variable to provide an accurate measurement of salt content.

SUMMARY OF THE INVENTION

Applicant has discovered that the measurement of salt content in the coating of a snack food can be measured accurately by utilizing backscattered X-rays with higher energy than the characteristic chlorine fluorescent X-rays. Because the backscatter X-rays have higher energy, the detector can be moved a larger distance away from the bed of snack food thus preventing any physical engagement between the detector and snack food. Further, it allows the use of a more rugged on-line salt analyzer because the measurement uses higher energy backscatter X-rays instead of low-energy chlorine X-rays. Such a more rugged on-line salt analyzer can be a Geiger counter which is relatively economical to purchase when compared to low-energy X-ray radiation detectors.

To further increase the accuracy of the detection, the low-energy chlorine X-rays can be blocked by using a mica or polymer window in the detector having a sufficient thickness to absorb the low-energy X-rays and leave only the high-energy X-rays for detection. For example, polypropylene with a thickness of 0.5 millimeter would absorb 99% of chlorine X-rays but less than 30% of backscatter X-rays.

With this type of detector, a system can be constructed wherein the output of the detector can be coupled to a processor comparator which compares a desired salt level signal with the actual salt level signal represented by the detected radiation and generates a signal to increase the amount of salt needed or to stop adding any salt until the proper salt concentration is obtained.

Thus it is an object of the present invention to provide on-line measurement of salt in snack foods by detecting high-energy backscatter X-rays instead of low-energy chlorine X-rays.

It is still another object of the present invention to provide a detector for measuring salt in snack foods by using high-energy backscatter X-rays to allow the detector to be moved a sufficient distance away from the snack food bed to prevent engagement of the detector with the snack foods if the snack foods do not maintain a substantially uniform layer.

It is also an object of the present invention to utilize a rugged on-line salt analyzer with a Geiger counter to measure the salt content because of the high-energy X-ray backscatter radiation detected.

It is yet another object of the present invention to provide a system for controlling the amount of salt or seasoning added to a snack food by detecting the amount of salt in the snack food, comparing the detected amount with a signal representing a desired amount, and controlling the amount of seasoning being coated on the snack foods in accordance with the signal from the comparator.

Thus the present invention relates to a non-destructive method for determining the salt content of snack foods by X-ray radiation backscatter including the steps of irradiating snack foods with X-ray radiation in the range of 4 keV to 12 keV, placing a detector of X-ray backscatter radiation above the snack food a distance of up to 8 inches and preferably in the range of from about 2 inches to about 8 inches, and detecting the X-ray backscatter radiation intensity from the snack food, the detected X-ray backscatter radiation intensity being representative of the snack food salt content.

The invention also relates to apparatus for non-destructive determination of the salt content of a snack food including an X-ray source for irradiating the snack food with low-energy X-ray radiation in the range of 4 keV to 12 keV, and a detector of the X-ray backscatter radiation located above the snack food at a distance in the range of 2 to 8 inches and adjusted for detecting the X-ray radiation backscatter intensity from the snack food and generating an output signal representing the intensity, the detected X-ray backscatter radiation intensity output signal being representative of the snack food salt content.

The invention also relates to a system for regulating the amount of salt or seasoning containing salt applied to a snack food.

BRIEF DESCRIPTION OF THE DRAWINGS

These and other features of the present invention will be more fully disclosed when taken in conjunction with the following DETAILED DESCRIPTION OF THE PREFERRED EMBODIMENT in which like numerals represent like elements and in which.

DETAILED DESCRIPTION OF THE PREFERRED EMBODIMENT

Figure 1:
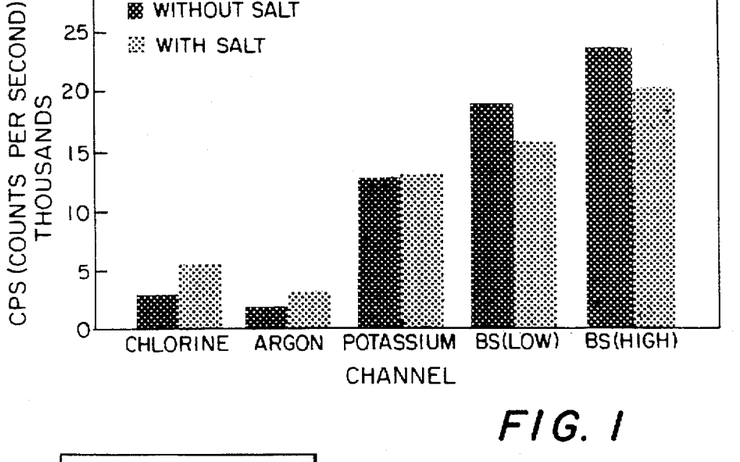
FIG. 1 is a graph of X-ray counts in different channels for unsalted and salted corn chips.
Figures 2, 4:
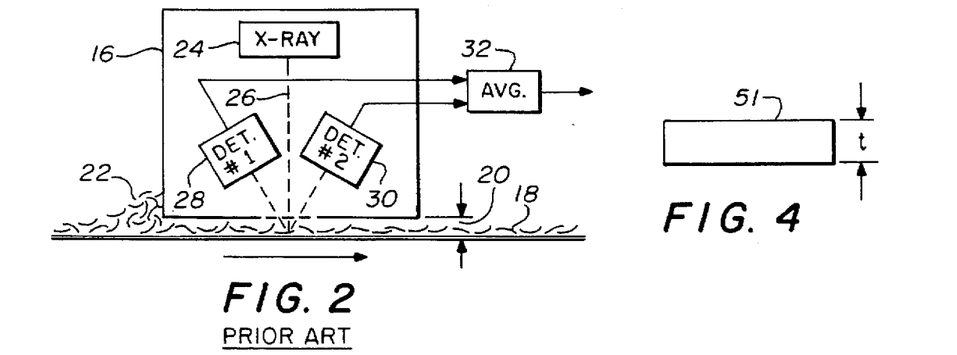
FIG. 2 is a schematic representation of a prior art system for measuring the salt content of a snack food utilizing measurements of the X-ray fluorescence of chlorine.
FIG. 4 illustrates a window of mica or polymer that can be placed in front of the detector and having a thickness, t, to further absorb and attenuate low-energy X-rays caused by chlorine X-ray fluorescence.

It is well known that when a substance is irradiated with X-rays, some of the X-rays will be absorbed by the substance and some will be backscattered from the substance (Compton and Rayleigh scattering). In addition, each element in the substance will emit X-ray fluorescence with characteristic energy. In low resolution energy dispersive X-ray analysis, X-rays are counted in channels by energy level. The channels are generally described by the element which has characteristic X-ray fluorescence with the same energy. FIG. 1 is a bar graph of X-ray intensities in different channels for unsalted and salted corn chips. When salt was added to corn chips, counts from chlorine X-ray fluorescence increased. In the prior art, salt content of snack foods has been measured by X-ray fluorescence of chlorine. Because chlorine X-rays have low energy (soft X-rays), the chlorine X-rays could be absorbed by the air if the detector were not very close to the product to which the X-rays are being applied. This requires, as will be seen in the schematic representation of the prior art detector in FIG. 2, that the detector 16 be placed very close to the bed 18 of the snack food on a continuously moving conveyor. The distance 20 has to be such that if the snack foods are not uniform and one happens to be on top of the other, they can engage the detector 16 as illustrated at 22 and thus cause a pile up or stack up of the snack foods thereby creating a problem with the automation process. The detector 16 includes an X-ray tube 24 that generates a flux of X-rays 26 that impinge upon the product 18. The chlorine X-rays are picked up by detectors 28 and 30 and coupled to an averaging circuit 32 where an average chlorine count level is obtained. That level can be compared with results of the well-known chloride titration with silver nitrate for samples and then the salt content adjusted accordingly. With this system, however, the chloride titration results must be manually performed on a regular interval and compared regularly with the detected amount of salt so that the proper salting or seasoning of the snack food can occur. The X-ray equipment 16 is extremely expensive inasmuch as it must detect the small amounts of low-energy chlorine X-rays. Further, as stated earlier, and as shown in FIG. 2, the detector 16 is so close to the bed of the snack food 18 that it is possible for the detector 16 to physically engage the snack food as shown at 22 in FIG. 2 and thus create a stack up of the snack foods, thereby interrupting the continuous on-line process.

It has always been assumed in the prior art that the backscattered X-rays could not be used as an accurate measurement of salt content in a snack food because backscatter would be too variable. Backscatter variation would be caused by variation in elemental composition of the seasoning (being applied to the snack food), physical size, content variation, and the like. FIG. 1 illustrates the possibility of measuring salt in snack foods from the backscattered X-rays. The decrease in backscatter (both backscatter with low energy and with higher energy) was almost as large as the increase in chlorine X-ray fluorescence caused by salt addition to corn chips. Both backscatter with low energy and with higher energy was reduced by salt addition to corn chips. Because salt measurement of snack foods by reduction in backscatter was not reported in the prior art, a number of tests were run to determine the correlation between backscatter and % salt in the product.

Figure 5:
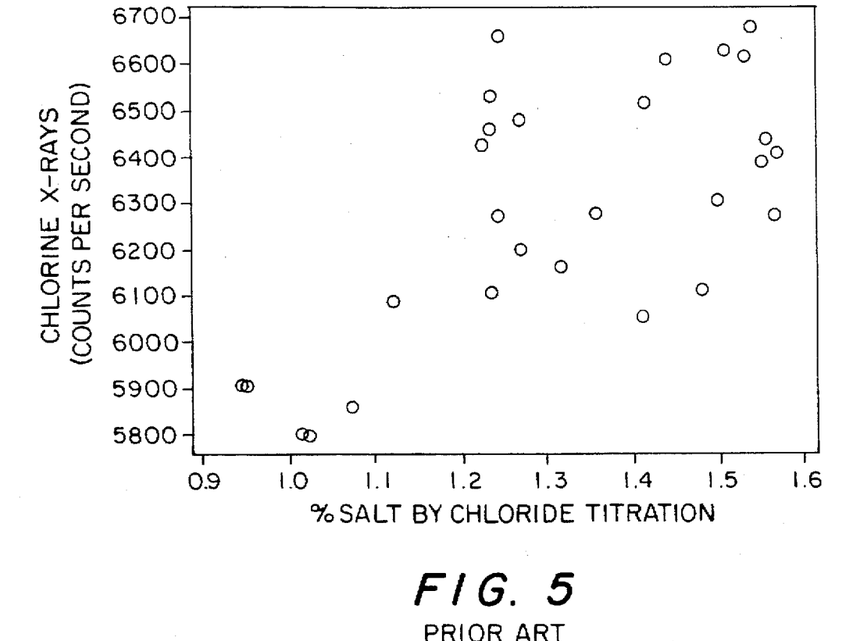
FIG. 5 is a graph of a plot of the detection of emitted photons from chlorine X-ray fluorescence versus the percent (%) salt for a seasoned corn chip.
Figure 6:
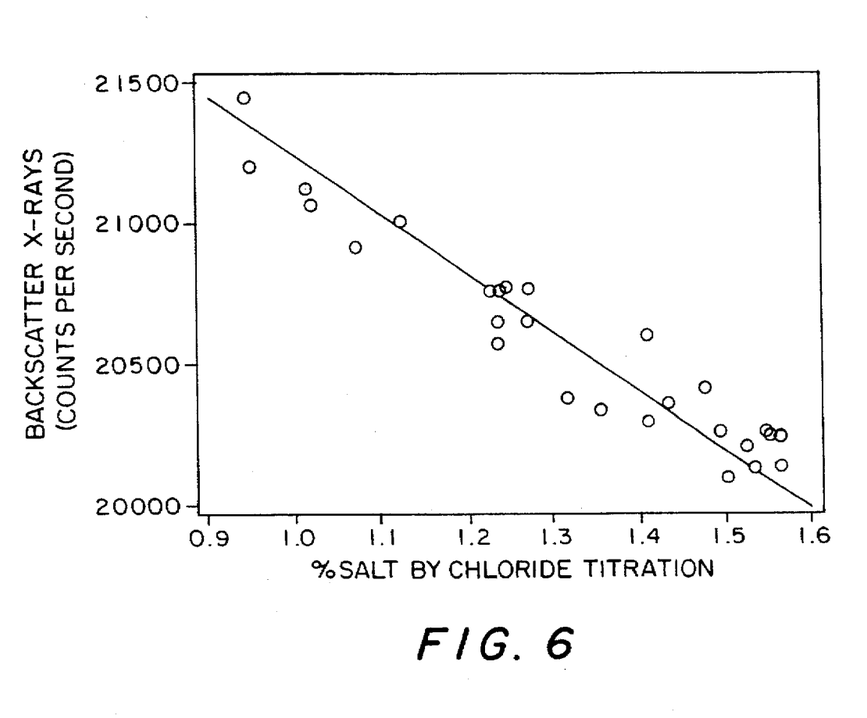
FIG. 6 is a graph illustrating the correlation between backscatter X-rays and percent (%) salt for a seasoned corn chip.

FIG. 5 is a graph illustrating a plot of characteristic chlorine X-rays versus the % salt. It will be noticed in FIG. 5 that the correlation shown is not good. The reason is because the plots have to be corrected for height of the detectors from the chip bed. That is not shown here, but when it is done the correlation is a reasonably good fit. This is the prior art method of chlorine X-ray fluorescence in which the chlorine re-emits photons and the counts detected are shown along the ordinate axis versus the % salt along the abscissa. FIG. 6 illustrates the correlation between the backscatter and % salt for salted corn chips. A low-energy X-ray source, preferably between 4 keV and 12 keV, is applied to the product. Since only the high-energy photons are being measured, the backscatter peak (high) in FIG. 1, it will be noted that a reasonably good correlation exists between the sampled points and the % salt.

Figure 7:
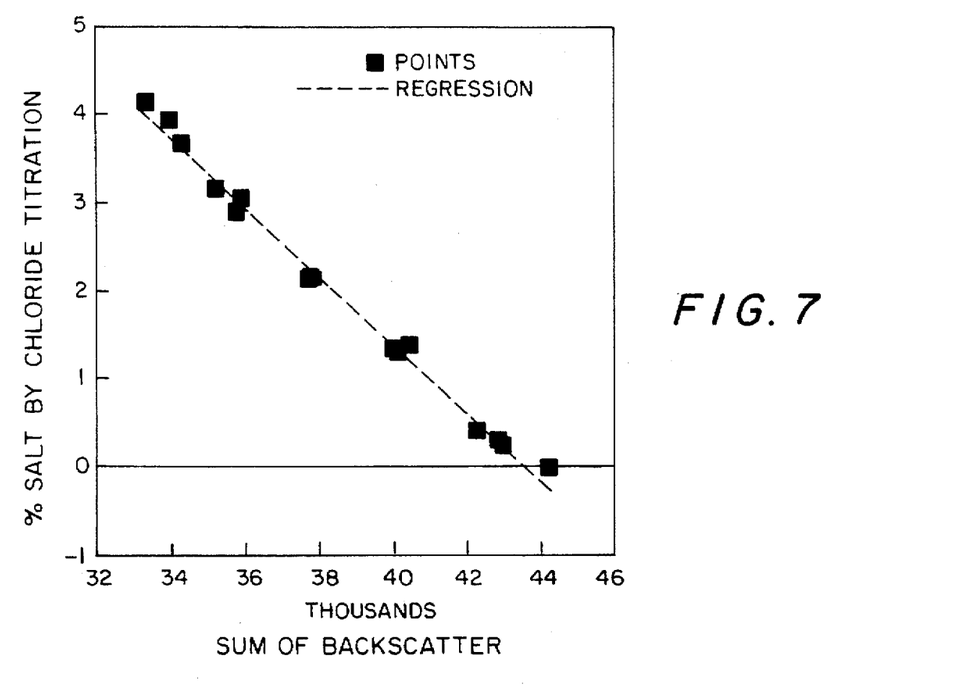
FIG. 7 is a graph of a correlation between backscatter X-rays and percent (%) of salt as determined by chloride titration.
Figure 8:
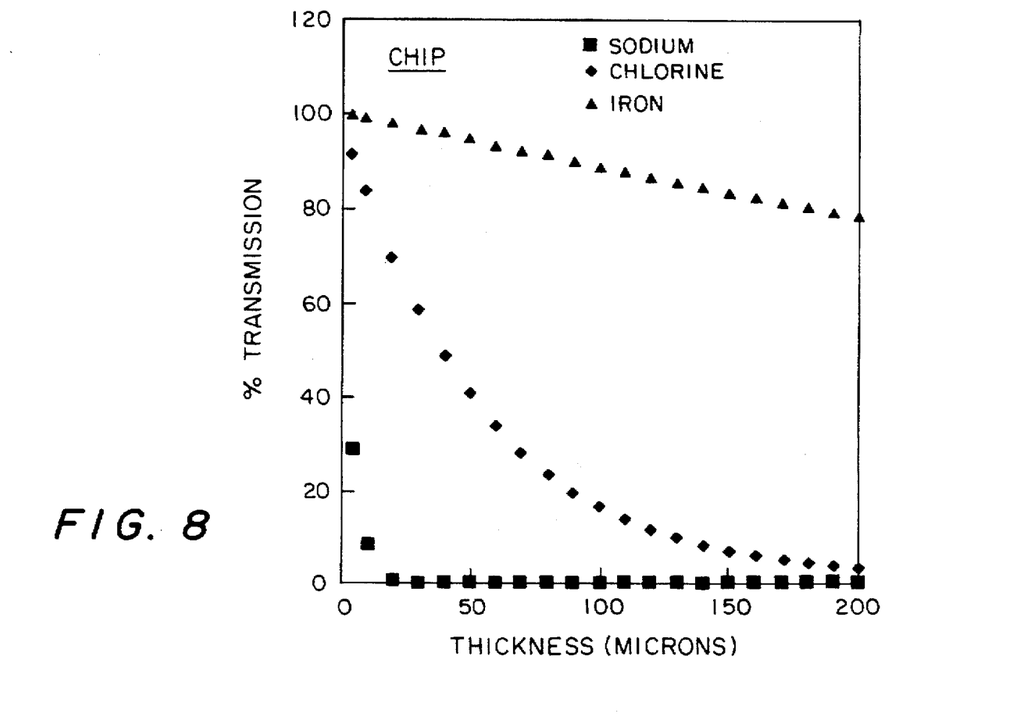
FIG. 8 is a graph of a comparison of the percent (%) of X-rays transmitted through a snack food for the characteristic X-rays of sodium, chlorine, and iron.

To further test the process, the results of percent (%) salt and the backscatter counts were compared. Percent salt was determined by chloride titration with silver nitrate, a procedure well known in the prior art that will not be described here. The results are shown in FIG. 7. Each of the squares represents a percentage of salt in a product, a salted corn chip, as determined by chloride titration. These salt percentages were plotted versus the readings for the backscatter counts with the best fit regression shown as a line. If the squares had formed a straight line, there would have been an exact correlation. It can be seen that the correlation is very close between the backscatter counts, and the actual percentage of salt as determined by chloride titration. Thus, this test illustrates that by measuring backscatter counts there is a remarkable correlation with the amount of salt in a product. However tests on other products were also conducted and while the correlation was not quite as good as illustrated in FIG. 7, the correlation was sufficiently good to enable this process to be used commercially to determine the percentage of salt contained by a particular product.

FIGS. 8, 9, 10, and 11 also illustrate why the measurement of backscatter provides a good correlation of the salt content of a particular product. FIGS. 8, 9, 10, and 11 were calculated from composition and mass absorption coefficients for X-rays using principles which are well known in the prior art. Backscatter X-rays would have approximately the energy of characteristic iron fluorescent X-rays because the X-ray tube has an iron target. As can been seen in FIG. 8, which is a plot of the calculated percent transmission of X-rays through a corn chip, it will be noted that for sodium there is almost no transmission after approximately 10 microns of thickness of product. Further, chlorine decreases very rapidly in transmission rate with thickness. However, note that backscattered radiation with the energy of characteristic iron X-rays decreases fairly slowly and uniformly with thickness. To measure chlorine X-rays, the detector must be close to the chip bed. If backscatter with approximately the energy of iron X-rays is used to measure salt, the analyzer head can be placed up to 8 inches above the snack food on the chip bed.

Figure 9:
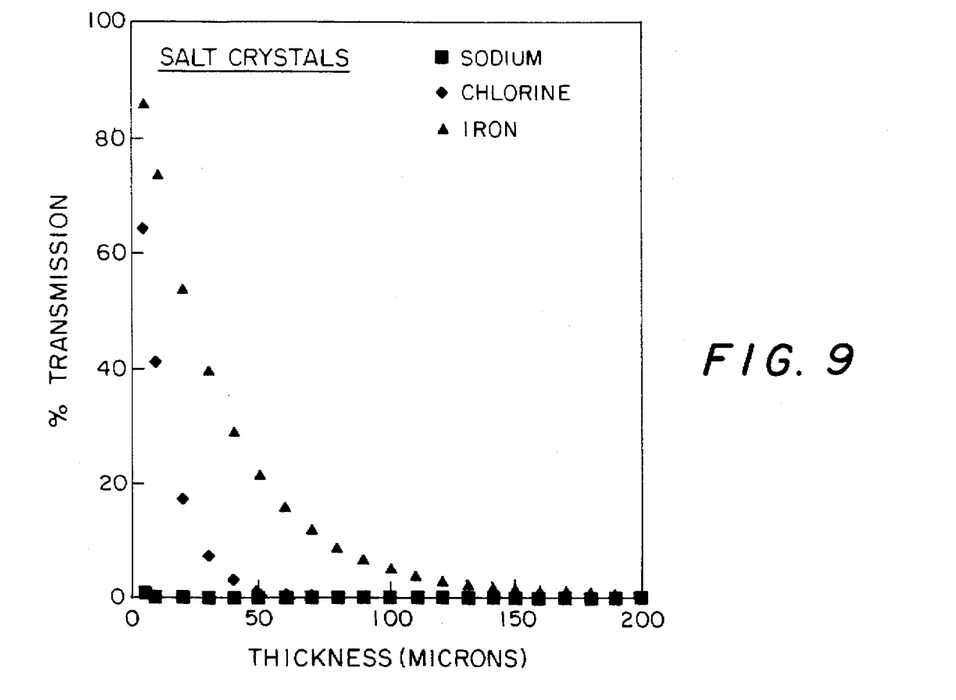
FIG. 9 is a graph of a comparison of the percent (%) of X-rays transmitted through salt crystals for the characteristic X-rays of sodium, chlorine, and iron.

FIG. 9 plots transmission versus thickness for salt crystals. Note that there is essentially no transmission, or in other words total absorption, by sodium at whatever thickness of the salt crystal. The chlorine transmission decreases very rapidly to zero at about 50 microns. The high-energy backscatter (iron) still has a 20% transmission at 50 microns of thickness.

Figure 10:
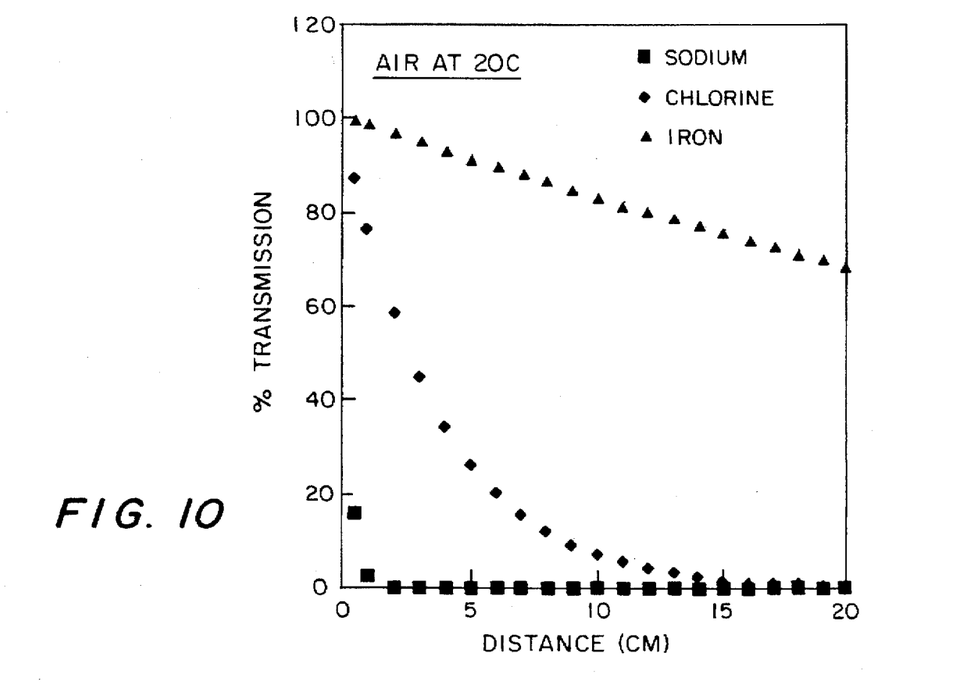
FIG. 10 illustrates the transmission of X-rays through air for the characteristic X-rays of sodium, chlorine, and iron.

FIG. 10 illustrates the transmission of X-rays through air. Note that sodium X-rays decrease to zero through essentially 2 centimeters of air. The transmission of chlorine X-rays decreases to 20% at 6 centimeters, while the transmission of backscatter (iron) radiation is still at 80% at approximately 11 centimeters distance. This means, of course, that the detector can be moved further from the sample with less loss due to transmission through air with higher energy backscatter (iron) X-rays.

Figure 11:
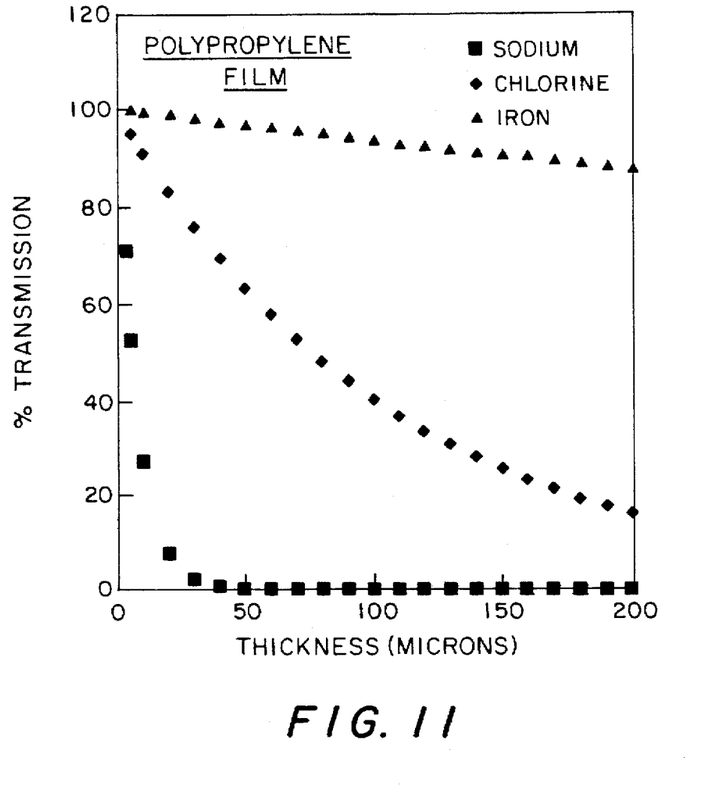
FIG. 11 illustrates the percent (%) transmission of X-rays through polypropylene film for the characteristic X-rays of sodium, chlorine, and iron.

FIG. 11 illustrates the percent transmission of X-rays through polypropylene film, which is used in some cases to protect the detectors. Note that with the sodium X-rays, it decreases to zero at 40 microns, the chlorine X-ray transmission decreases to approximately 20% at 200 microns, while the high-energy intensity level of iron X-rays remain at 90% at 200 microns. Chlorine X-rays required thin polypropylene windows to separate the detector from the product. The analyzer currently uses 6.3 micron film. With backscatter based measurement, the film could be considerably thicker because the backscatter X-rays with higher energy are less absorbed by the polypropylene. These graphs all illustrate the importance of using higher energy backscatter X-rays rather than the lower energy chlorine fluorescence radiation.

Figure 12:
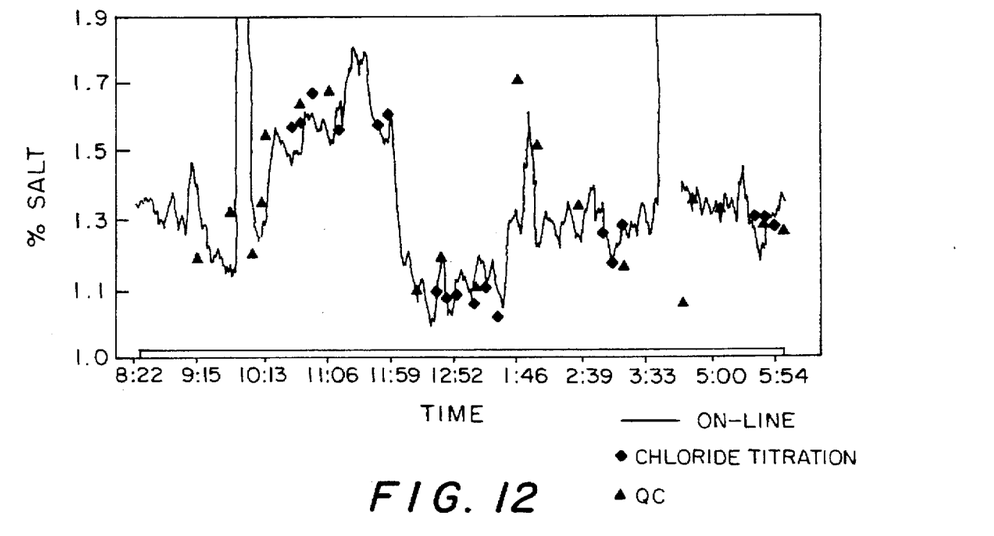
FIG. 12 is a graph of an independent test of the salt content of a seasoned corn chip with the on-line system of the present invention.

FIG. 12 is a graph of an independent test of the salt content on salted corn chips with the on-line system of the present invention, chloride titration results, and quality control tests performed with a laboratory bench-top X-ray fluorescence analyzer. The results shown are extremely good, particularly considering that this was a relationship that did not include a distance correction. Clearly, the correlation between backscatter and % salt is very accurate. The on-line reading was high about 10:00 a.m. and about 3:30 p.m. because the manufacturing line was briefly shut down.

Figure 3:
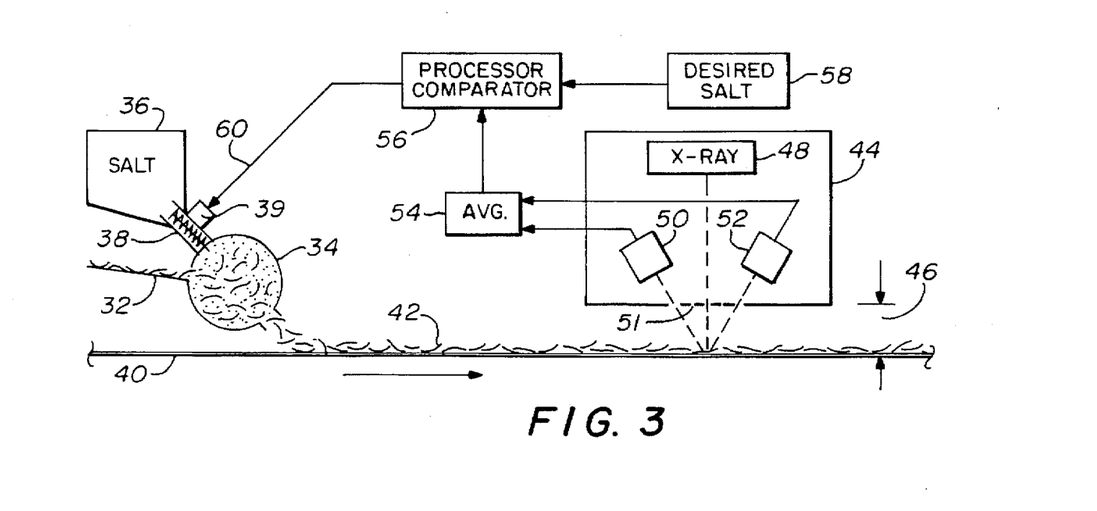
FIG. 3 is a schematic representation of a system of the present invention for regulating the amount of seasoning containing salt applied to snack foods including a novel X-ray detection unit that measures high-energy backscatter X-rays instead of low-energy chlorine X-rays.

A system for regulating the amount of salt containing seasoning applied to snack foods is illustrated in FIG. 3. A continuously moving conveyor 40 has snack food 42 applied thereon in a substantially uniform layer. A seasoning applying device 34 receives snack food by conveyor 32 and has applied thereto a substantially uniform coating of salt containing seasoning from a source such as bin 36 applied by an auger 38. The seasoning applying device 34 is well known in the art, and may be, for instance, a rotating drum that causes the seasoning to be applied to the snack food in a substantially uniform coating over the entire surface and then deposits the seasoned snack food 42 on the continuously moving conveyor 40 in the substantially uniform layer as shown. A seasoning regulating device 38, which is also well known in the art and may be, for instance, an auger driven by motor 39, adjusts the amount of seasoning applied to the snack foods. A device 44 for irradiating the snack foods with X-ray radiation includes an X-ray source 48 and detectors 50 and 52. The X-rays from source 48 are from 4 keV to 12 keV and impinge upon the snack foods. Those X-rays that do not pass through the snack food or are not absorbed by the salt and other elements thereon are backscattered and detected by the detectors 50 and 52 in a manner well known in the art. As stated earlier, backscatter counts are measured by detectors 50 and 52. Again, the window 51 in the device 44 and shown in FIG. 4 may be of a thickness, t, or formed of a substance such as mica that will absorb almost all of the chlorine X-rays while transmitting most of the backscatter X-rays. The counts from the detectors 50 and 52 are averaged in circuit 54 and are coupled to a comparator 56. A memory 58 stores a count for a desired salt content on the chips which is compared to the signal representing the actual salt content measurement from the averaging circuit 54. The comparator 56 then produces an output on line 60 whenever additional salt is needed to power motor 39 and drive the auger 38 and to provide no output signal on line 60 when the salt is sufficient. The rotation of auger 38 ceases thus stopping the application of salt or a seasoning containing salt to the snack foods in the rotating drum 34 (seasoning applying drum). The detectors 50 and 52 are located in the device 44 which is positioned above the snack food at a distance 46 in the range of up to about 2 to 8 inches. This prevents any contact physically with the snack foods 42 and prevents any jamming as illustrated with prior art devices in FIG. 2. This distance of the detector above the snack foods at a distance of 2 to 8 inches is possible because the backscatter X-rays are only slightly absorbed by air. The processor comparator 56 and the memory 58 along with the averaging circuit 54 provide circuit means coupled between the detectors 50 and 52 and the seasoning regulating device or auger 38 for automatically adjusting the amount of seasoning applied to the snack foods based on the detected intensity of the X-ray radiation backscatter. Again, the memory 58 stores a signal representing a desired X-ray backscatter radiation level for a given desired salt level on the snack foods and the processor comparator 56 that is coupled to the memory 58 and the detector averaging circuit 54 makes the desired comparison and generates the necessary output signals to the seasoning regulating device such as auger 38 for causing more or less seasoning to be applied to the snack foods in accordance with the detector output signal. A motor 39 is shown in FIG. 3 schematically coupled to the auger 38 to rotate the auger to carry the salt or seasoning containing salt from bin 36 (source of seasoning) into the seasoning applying device 34 in a well-known manner.

The detectors 50 and 52 of device 44 may be Geiger counters that are of much lower cost than the prior art detector that must be more sensitive to the detection of X-rays from chlorine fluorescence.

The window 51 shown in FIG. 4 may be polypropylene placed between the backscattered radiation and the detectors 50 and 52. The polypropylene is of a sufficient thickness, t, to substantially block chlorine X-rays but transmits most backscatter X-rays. As stated earlier, the window 51 may be formed of mica.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

I claim

1. A non-destructive method for determining the salt content of snack foods exposed to ambient air on a support base by measuring backscatter X-rays including the steps of:

irradiating the snack foods with X-ray radiation in the range of from about 4 keV to about 12 keV;

placing a detector of X-ray backscatter energy level radiation above the snack food a distance ranging from 2 inches up to about 8 inches to prevent physical contact with the snack food;

detecting the X-ray backscatter radiation energy level intensity from said snack food at an energy level intensity above the energy level of chlorine X-rays, said detected X-ray backscatter radiation intensity being representative of the snack food salt content; and determining said snack food salt content solely from said backscatter radiation.

2. The method of claim 1 further including the steps of:

depositing said snack food on a continuously moving conveyor in a substantially uniform layer where said detector distance above said snack food serves to prevent piling or stacking up of said snack foods against the X-ray detector as said snack food moves past said detector;

subjecting at least a portion of said snack food on said continuously moving conveyor to X-ray radiation; and detecting the X-ray backscatter radiation from said snack food on said moving conveyor such that an ongoing determination of the salt content of said snack food is provided.

3. The method of claim 2 further including the step of using a Geiger counter as the X-ray backscatter radiation detector.

4. The method of claim 2 further including the step of substantially blocking X-ray radiation to said detector that is generated at and below the energy level of chlorine X-rays.

5. The method of claim 4 further including the step of placing a window of polypropylene between backscattered radiation and said detector, said window of polypropylene being of a sufficient thickness, t, to substantially block the X-rays from chlorine fluorescence.

6. The method of claim 4 further including the step of placing a window formed of mica between said backscattered radiation and said detector, said mica being of sufficient thickness to substantially block the X-rays from chlorine fluorescence.

7. Apparatus for non-destructive determination of the salt content of a snack food exposed to ambient air on a support base including:

an X-ray source for irradiating the snack food with X-ray radiation in the range of from about 4 keV to about 12 keV;

a detector of X-ray backscatter radiation energy level located above the snack food at a distance in the range of from about 2 inches up to about 8 inches to prevent physical contact with the snack food and adjusted for detecting the X-ray radiation energy level intensity from such snack food only at an energy level intensity above the energy level of chlorine X-rays and generating an output signal representing said energy level intensity; and said detected X-ray backscatter radiation energy level intensity output signal being solely representative of the snack food salt content.

8. Apparatus as in claim 7 further including:

a continuously moving conveyor having said snack food thereon in a substantially uniform layer;

said X-ray source being positioned to irradiate at least a portion of said snack food on said continuously moving conveyor; and said detector of X-ray backscatter radiation providing an ongoing determination of the salt content of said snack food on said continuously moving conveyor.

9. Apparatus as in claim 8 further including a Geiger counter used as said detector of said X-ray backscatter radiation.

10. Apparatus as in claim 8 further including means for substantially blocking X-ray radiation to said detector that is generated by chlorine fluorescence.

11. Apparatus as in claim 10 wherein said X-ray blocking means comprises a window of polypropylene placed between said backscattered radiation and said detection, said window of polypropylene being of a sufficient thickness, t, to substantially block the X-ray radiation generated by chlorine fluorescence.

12. Apparatus as in claim 10 wherein said X-ray blocking means comprises a window formed of mica and placed between said backscattered radiation and said detector, said mica being of sufficient thickness to substantially block the X-ray radiation generated by chlorine fluorescence.

13. A system for regulating the amount of salt containing seasoning applied to snack foods including:

a continuously moving conveyor having said snack food thereon in a substantially uniform layer;

a seasoning applying device for receiving said snack food and applying a substantially uniform coating of salt-containing seasoning to said snack food and depositing said seasoned snack food on said continuously moving conveyor in said substantially uniform layer;

a seasoning regulating device attached to such seasoning applying device for adjusting the amount of seasoning applied to said snack foods;

an X-ray source for irradiating the snack food with X-ray radiation in the range of from about 4 keV to about 12 keV;

a detector of X-ray backscatter radiation located above the snack food at a distance in the range of from about 2 inches up to about 8 inches and adjusted for detecting the X-ray radiation backscatter intensity from said snack food only at an energy level above the energy level of chlorine X-rays and generating an output signal representing said intensity, said detected X-ray backscatter radiation intensity output signal being solely representative of the snack food salt content; and a circuit coupled between said detector and said seasoning regulating device for automatically adjusting the amount of seasoning applied to said snack foods based upon the detected intensity of the X-ray radiation backscatter.

14. The system of claim 13 wherein said circuit includes:

a memory for storing a signal representing a desired X-ray backscatter radiation level for a given desired salt level on such snack foods;

a comparator coupled to said memory and said detector for comparing the signal stored in said memory with said detected X-ray backscatter radiation level; and said comparator generating output signals to said seasoning regulating device for causing more or less seasoning to be applied to said snack food in accordance with said detector output signal.

15. A system as in claim 14 further including:

an auger immersed in seasoning as said seasoning regulating device;

a drive source coupled to said auger for rotating said auger to carry salt containing seasoning into such seasoning applying device; and said comparator being coupled to said drive source to drive said auger only when more salt is required on said snack food as determined by said X-ray backscatter radiation intensity.

16. A system as in claim 13 wherein said detector is a Geiger counter.

17. A system as in claim 13 further including radiation absorbing means for substantially blocking X-ray radiation to said detector that is generated by chlorine fluorescence.

18. A system as in claim 17 wherein said radiation absorbing means for blocking X-ray radiation to said detector is a window of polypropylene placed between said backscattered radiation and said detector, said window of polypropylene being of substantial thickness to substantially block X-ray radiation generated by chlorine fluorescence.

19. A system as in claim 17 wherein the radiation absorbing means for blocking X-ray backscatter radiation to said detector is a window formed of mica placed between said backscattered radiation and said detector, said mica being of sufficient thickness to substantially block X-ray radiation generated by chlorine fluorescence.

* * * * *